(12) United States Patent
Schmitz et al.

(10) Patent No.: US 6,647,093 B2
(45) Date of Patent: Nov. 11, 2003

(54) METHOD AND DEVICE FOR THE PROCESSING OF X-RAY IMAGES

(75) Inventors: Georg Schmitz, Wachtberg (DE); Henning Braess, Aachen (DE); Harald Reiter, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/084,758

(22) Filed: Feb. 25, 2002

(65) Prior Publication Data

US 2002/0150211 A1 Oct. 17, 2002

(30) Foreign Application Priority Data

Feb. 28, 2001 (DE) .......................... 101 09 586

(51) Int. Cl.[7] .................................. H05G 1/44
(52) U.S. Cl. ..................................... 378/108
(58) Field of Search ..................... 378/97, 98, 98.12, 378/108, 98.9

(56) References Cited

U.S. PATENT DOCUMENTS

| | | | | |
|---|---|---|---|---|
| 4,335,311 A | * | 6/1982 | Lutz et al. ................ | 378/108 |
| 4,980,905 A | * | 12/1990 | Meccariello .............. | 378/207 |
| 5,022,063 A | * | 6/1991 | Yokouchi et al. ......... | 378/98.2 |
| 5,289,373 A | | 2/1994 | Zarge et al. .............. | 364/413.13 |
| 6,198,834 B1 | * | 3/2001 | Belk et al. ................ | 382/110 |
| 6,490,337 B1 | * | 12/2002 | Nagaoka et al. .......... | 378/20 |

* cited by examiner

Primary Examiner—Max Noori

(57) ABSTRACT

The invention relates to a method and a device for the processing of X-ray images which can be used notably in medical fluoroscopy procedures since they keep the overall radiation load for a patient low. Processing of and detail enhancement in the X-ray images is preferably performed by means of a pattern matching algorithm which necessitates prior knowledge of a pattern of the detail of interest. In order to extract this pattern, at least one single image (HD) is formed (2) with a higher dose rate, said single image having an image quality which suffices for the automatic (4) or non-automatic (3) recognition of the pattern. The information extracted from this single image serves as a basis for the evaluation of X-ray images (LD2) formed with a lower dose rate.

15 Claims, 1 Drawing Sheet

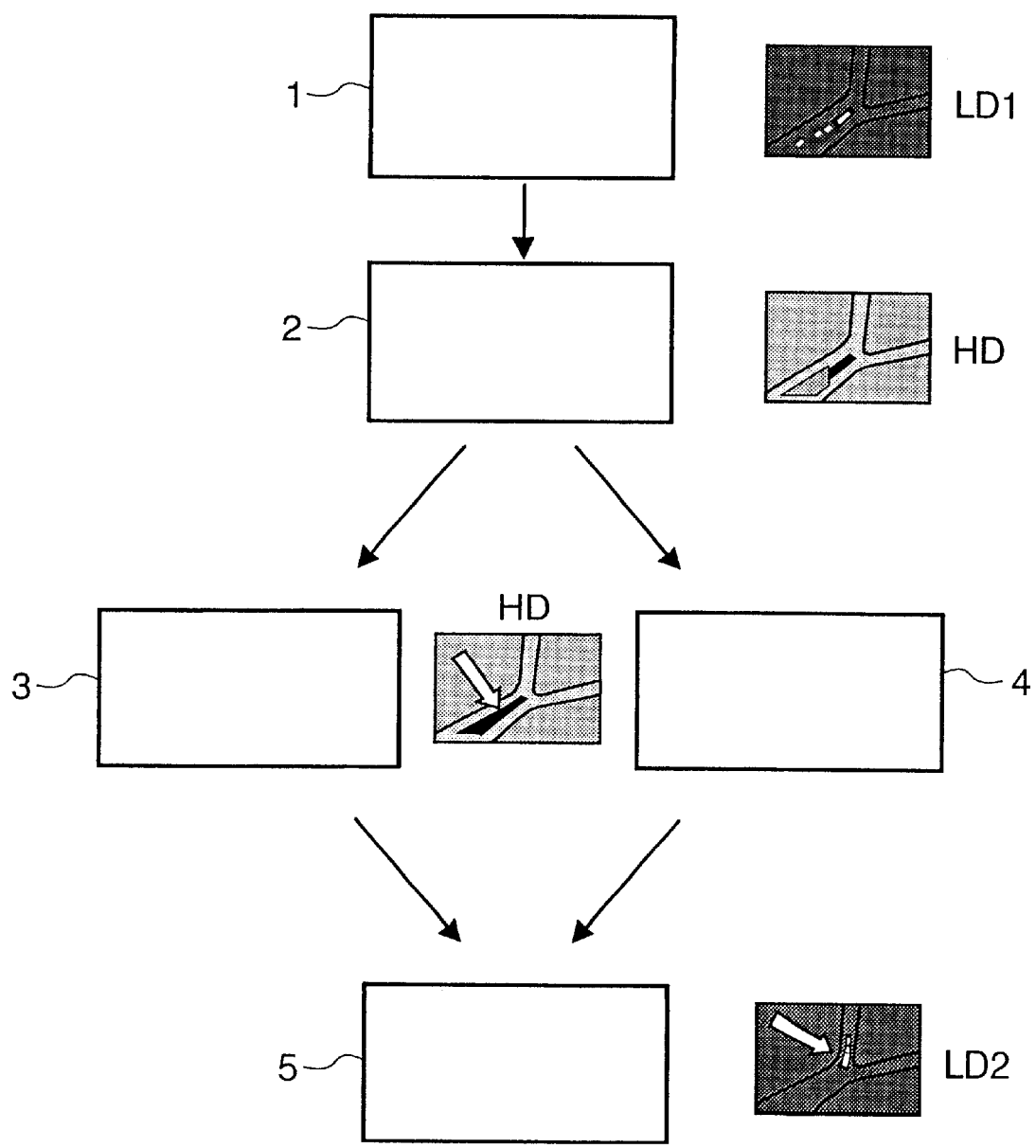

METHOD AND DEVICE FOR THE PROCESSING OF X-RAY IMAGES

The invention relates to a method for the processing of X-ray images and to a device for carrying out such a method.

Generally speaking, the signal-to-noise ratio, and hence the image quality, of fluoroscopic images of objects that have been acquired by means of X-rays is higher as the dose rate of the X-rays used is higher. For these reasons per se it would be desirable to use high dose rates for the acquisition of X-ray images; however, the radiation load for the object to be examined is thus increased. This holds notably for the formation of medical X-ray images of a patient for whom the radiation load is to be kept as small as possible for reasons of health. In particular in the case of fluoroscopic examinations, where images of a patient are formed and displayed on a display screen at a repetition rate of typically 30 images per second, the dose rate used should be limited to acceptable values. In order to derive a maximum amount of information from the acquired X-ray images nevertheless, therefore, as effective as possible algorithms are used for the image processing so as to suppress disturbing effects and achieve enhanced reproduction of the details of interest.

For example, U.S. Pat. No. 5,289,373 describes a method of recognizing and highlighting a guide wire on a fluoroscopic display screen, which guide wire emanates from a catheter introduced into the vascular system of a patient. Using the algorithm, an image region in which the guide wire should be situated is automatically inspected; first the pixels are determined in which local extremes of the grey values occur and after that it is determined which of those pixels yield a coherent line which could correspond to the guide wire.

The algorithm which is known from U.S. Pat. No. 5,289,373 does not require information concerning the detail "guide wire" to be displayed other than the general facts that the guide wire is formed by a shadow (extreme gray value) and that it must constitute a coherent line. Because objects other than the relevant guide wire may also satisfy these criteria, the algorithm involves the risk of identifying the wrong structure as the guide wire. Furthermore, it may occur that the algorithm cannot locate the guide wire, because it does not satisfy, by way of exception, the relevant criteria in the special image formed. In order to enhance the probability of correct detection of the guide wire by the algorithm, therefore, it is advantageous when the user can limit the region to be searched as much as possible.

Furthermore, for the recognition of given objects or structures there have been developed effective algorithms which utilize a predetermined pattern of the structure to be recognized. In an X-ray image the algorithms search for the positions which best match the predetermined pattern. Because of this procedure, such algorithms are also referred to as "pattern matching algorithms". Such algorithms, however, have the drawback that they require a pattern of the desired detail which is not always available or not always available in the same form, that is, notably in the case of dynamic objects such as a guide wire which is moved through the body.

Considering the foregoing it was an object of the present invention to provide a method and a device for the processing of X-ray images which minimize the X-ray dose rate used and offer at the same time a suitable recognition performance and image enhancement for details of interest.

In conformity with the method for the processing of X-ray images, notably medical X-ray images acquired by fluoroscopy, at least one X-ray image is formed with a dose rate which is higher than the dose rates used to form the other images. Therefore, this image has a better signal-to-noise ratio or a higher image quality. This single image of higher image quality is then used as a basis for the algorithm for the processing of the other (previous and/or notably subsequent) images.

Overall the method in accordance with the invention can be performed while utilizing a smaller radiation load for the object to be examined; notably a patient who is subjected to fluoroscopy, because the vast majority of the X-ray images is formed with a low dose rate. Single images with a higher dose rate are formed only once or only a comparatively small number of times. Typically, such a single image is followed by several hundred or even a thousand normal X-ray images with a lower dose rate. The increased dose rate of the single images, therefore, is hardly of significance for the total radiation load. For the processing of all X-ray images, however, the single images present a significant improvement because of their high quality. Notably information which is not present in the normal images and which enables the relevant image processing algorithm to evaluate the normal X-ray images better can be derived from such single images.

Notably a pattern matching algorithm is used as the algorithm for the image processing; this algorithm utilizes at least one pattern of the image detail to be displayed, that is, the image detail of interest, for example, a guide wire. This pattern can then be derived from the single images acquired with a higher dose rate, so that a comparatively up-to-date and exact pattern is always available in dynamic situations also.

In conformity with a preferred version of the method, the pattern matching algorithm can additionally apply an automatic pattern recognition procedure so as to extract the pattern necessary for the processing of images with a lower dose rate from the single image with a higher dose rate. The pattern required, therefore, need not be entered in the algorithm with advance knowledge, but can be extracted by the algorithm itself from the presented images with a higher dose rate. This is advantageous notably in dynamic situations in which the shape of the pattern to be recognized changes continuously. An example in this respect is the tracking of a stent or of the guide wire of a catheter in medical X-ray fluoroscopy.

Alternatively, or additionally, the pattern matching algorithm may be provided with an input interface via which the pattern required for the processing of images with a lower dose rate can be entered after extraction of this pattern from an X-ray image with a higher dose rate. The external extraction of the pattern to be entered can be performed, for example, by the attending physician. Human knowledge and human capability of recognition can thus be introduced into the pattern matching algorithm for the benefit of the subsequent evaluations of "normal" X-ray images.

Furthermore, the method may be arranged so that the image processing of X-ray images with a lower dose rate is concentrated on regions of the image in which a detail to be reproduced was detected in the X-ray image with a higher dose rate. Using the single image of higher quality, a region of interest (ROI) can thus be defined automatically, or externally by a user, after which the further attention is focused on said region of interest. For various reasons the algorithms used for image processing can yield a better performance when they are limited to the regions which are really of interest. Not in the least a smaller region can be treated faster, thus leaving more time for more exact image processing in the case of real-time methods, for example, for the execution of a number of iterations. The reproduction of the region of interest can also be improved, for example, when the local histogram of the grey values is stretched across the display spectrum of the monitor used.

The instant at which a single image is formed with a higher dose rate is formed, can be externally specified by a user. For example, a physician can trigger the formation of such an image when he or she knows that the position of a catheter has changed significantly since the last single image. However, it is also possible to form an X-ray image with a higher dose rate automatically when a performance criterion which is a measure of the quality or reliability of the relevant image processing operation drops below a given threshold. For example, when the result of the pattern matching algorithm becomes inadequate, a new single image with a higher dose rate can be formed so as to provide the pattern matching algorithm once more with a new underlying pattern.

The invention also relates to a device for the processing of digitized X-ray images, which device may notably be a device for performing fluoroscopy on a patient for medical purposes. The device includes a central processor which is arranged in such a manner that it can carry out a method of the kind set forth. This means that the central processor can access the digitized X-ray images and process these images by way of a suitable method such as in particular a pattern matching algorithm. Furthermore, the central processor is arranged in such a manner that it can utilize single images which have been formed with a dose rate higher than that used for the other images as a basis for the algorithm used. For example, the pattern utilized by a pattern matching algorithm can be automatically detected in the single images with a higher dose rate, or the region of interest on which the subsequent image processing by the central processor should be concentrated can be detected therein.

Furthermore, the central processor may be connected to the control system of an X-ray imaging apparatus in such a manner that it can request said control system to form an X-ray image with a higher dose rate. For example, when the results of the image processing no longer meet a specified quality standard, the central processor may apply a request signal to the X-ray imaging apparatus; in response thereto the X-ray apparatus forms a single image with a higher dose rate and hence a better quality.

The invention will be described in detail hereinafter, by way of example, with reference to the FIGURE. The sole FIGURE shows a flow chart illustrating a method in accordance with the invention for the processing of X-ray images.

The method illustrated in FIG. 1 can be advantageously used in the field of processing of medical X-ray fluoroscopic images. Notably the aspect of visibility of small details such as, for example, guide wires and stents is then concerned. The method enables the use of the particularly effective pattern matching algorithms for which it is necessary that the appearance of the image detail to be enhanced is known. Examples of such algorithms are described in I. Kompatsiaris et al.: "Deformable Boundary Detection of Stents in Angiographic Images", IEEE Transact. on Medical Imaging, Vol. 19, No. 6, June 2000, pp. 653 to 662, as well as in G. L. Turin: "An Introduction to Matched Filtering", IRE Trans. on Inform. Theory (June 1960), pp. 311 to 329.

For medical applications in particular the dose rates used to form the X-ray images have to be limited severely in order to minimize the radiation load for the patient. The X-ray images then formed, therefore, contain a large amount of noise and hence have a correspondingly low image quality, so that said particularly effective algorithms cannot simply be applied thereto.

In order to solve this problem the method in accordance with the invention proposes the formation of a single image with a higher dose rate when required, said single image having an image quality which suffices so as to serve as a basis for evaluation algorithms.

The FIGURE shows, by way of example, the situation where the movement of a catheter or a guide wire in the body of the patient is to be tracked. In the step 1 of the method the attending physician can indicate that the quality of the images LD1 with a low dose rate no longer suffices and that image enhancement or recognition of a new detail of the object is desired. Subsequently, in the step 2 a single image HD is formed with a higher dose rate; this image thus contains little noise and hence has a higher image quality. The desired details usually can be suitably recognized in this image.

In conformity with a first alternative, in the step 3 the physician can indicate exactly which structures are of interest in the single image HD formed. This information is then used in the step 5 so as to recognize this detail again in later X-ray images LD2 formed with a lower dose rate. Notably the above-mentioned matched filter techniques are applied for this purpose.

As an alternative to the step 3, or as a supplement, in the step 4 an automatic pattern recognition operation can also be performed on the single image HD of enhanced quality. Because the single image is of a high quality, it is possible to apply algorithms which are not robust in respect of noise and hence are not suitable for conventional fluoroscopic images LD1, LD2.

The knowledge derived from the single image HD of enhanced quality can thus be advantageously used in the step 5 of the method so as to enhance the detail on the basis of the knowledge of the detail.

Furthermore, in subsequent images LD2 the processing can be limited to a region of interest (ROI) so as to enhance the reproduction in this region in which the object of interest, for example a guide wire, is situated at the relevant instant. For example, the local histogram of the grey values can be stretched for this region.

What is claimed is:

1. A method for the processing of X-ray images, the method comprising the steps of:

forming at least one X-ray image with a first dose rate which is higher than a second dose rate used to form at least one other image;

using the at least one X-ray image to process the at least one other image; and performing image processing using a pattern matching algorithm which utilizes at least one pattern of an image detail to be reproduced, wherein the pattern matching algorithm utilizes an automatic pattern recognition procedure for deriving the pattern required for the processing of the at least one other image with the second dose rate from the at least one X-ray image with the first dose rate.

2. A method as claimed in claim 1, wherein the image processing of the at least one other image with the second dose rate is concentrated on an image region in which a detail to be reproduced was detected in the at least one X-ray image (HD) with the first dose rate.

3. A method as claimed in claim 1, wherein the at least one X-ray image is formed with the first dose rate when a performance criterion of an algorithm used for image processing drops below a predetermined threshold.

4. A device for the processing of a plurality of digitized X-ray images, which device includes a central processor which is arranged so as to carry out a method as claimed in claim 1.

5. A device as claimed in claim 4, wherein the central processor is connected to a control system of an X-ray imaging apparatus in such a manner that the control system can be requested to form the at least one X-ray image with the first dose rate.

6. A device for the processing of a plurality of digitized X-ray images, which device includes a central processor which is arranged so as to carry out a method as claimed in claim 2.

7. A device for the processing of a plurality of digitized X-ray images, which device includes a central processor which is arranged so as to carry out a method as claimed in claim 3.

8. A method for the processing of X-ray images, the method comprising the steps of:

forming at least one X-ray image with a first dose rate which is higher than a second dose rate used to form at least one other image;

using the at least one X-ray image to process the at least one other image; and performing image processing using a pattern matching algorithm which utilizes at least one pattern of an image detail to be reproduced, wherein the pattern matching algorithm comprises an input interface via which the pattern required for the processing of the at least one other image with the second dose rate can be entered after its extraction from the at least one X-ray image with the first dose rate.

9. A method as claimed in claim 8, wherein the image processing of the at least one other image with the second dose rate is concentrated on an image region in which a detail to be reproduced was detected in the at least one X-ray image (HD) with the first dose rate.

10. A method as claimed in claim 9, wherein the at least one X-ray image is formed with the first dose rate when a performance criterion of an algorithm used for image processing drops below a predetermined threshold.

11. A method as claimed in claim 8, wherein the at least one X-ray image is formed with the first dose rate when a performance criterion of an algorithm used for image processing drops below a predetermined threshold.

12. A device for the processing of a plurality of digitized X-ray images, which device includes a central processor which is arranged so as to carry out a method as claimed in claim 8.

13. A device for the processing of a plurality of digitized X-ray images, which device includes a central processor which is arranged so as to carry out a method as claimed in claim 9.

14. A device for the processing of a plurality of digitized X-ray images, which device includes a central processor which is arranged so as to carry out a method as claimed in claim 10.

15. A device for the processing of a plurality of digitized X-ray images, which device includes a central processor which is arranged so as to carry out a method as claimed in claim 11.

* * * * *